(12) United States Patent
Hedberg

(10) Patent No.: US 8,555,520 B2
(45) Date of Patent: Oct. 15, 2013

(54) ACCELERATED EVAPORATION PROCESS AND APPARATUS UTILIZING RE-CIRCULATING LOOPS

(75) Inventor: Herbert J. Hedberg, N. Attleboro, MA (US)

(73) Assignee: Harvard Bioscience, Inc., Holliston, MA (US)

( * ) Notice: Subject to any disclaimer, the term of this patent is extended or adjusted under 35 U.S.C. 154(b) by 481 days.

(21) Appl. No.: 12/823,720

(22) Filed: Jun. 25, 2010

(65) Prior Publication Data

US 2010/0326604 A1    Dec. 30, 2010

Related U.S. Application Data

(60) Provisional application No. 61/220,236, filed on Jun. 25, 2009.

(51) Int. Cl.
*F26B 5/08* (2006.01)
(52) U.S. Cl.
USPC .......... 34/381; 34/413; 34/60; 34/75; 118/52; 118/320; 427/240; 427/425; 366/241; 422/553
(58) Field of Classification Search
USPC .......... 34/312, 381, 413, 497, 60, 75, 58, 90; 62/555; 118/52, 320; 427/240, 425; 366/208, 219, 241; 422/552, 553
See application file for complete search history.

(56) References Cited

U.S. PATENT DOCUMENTS

| | | | | |
|---|---|---|---|---|
| 2,184,100 | A | * | 12/1939 | Mondloch ........................ 134/62 |
| 2,361,894 | A | * | 10/1944 | Williams ........................ 210/184 |
| 2,561,395 | A | * | 7/1951 | Marshall ........................ 159/4.01 |
| 4,580,901 | A | * | 4/1986 | Goldsmith ........................ 356/409 |
| 5,477,623 | A | * | 12/1995 | Tomizawa et al. ................ 34/58 |
| 6,451,261 | B1 | * | 9/2002 | Bodner et al. ................ 422/569 |
| 6,716,285 | B1 | * | 4/2004 | Weyburne et al. ............... 118/52 |
| 6,783,732 | B2 | * | 8/2004 | Madden et al. ................ 422/63 |
| 7,081,600 | B2 | * | 7/2006 | Brown et al. ................ 219/428 |
| 2003/0079365 | A1 | * | 5/2003 | Corak et al. ........................ 34/89 |
| 2004/0029258 | A1 | * | 2/2004 | Heaney et al. ............ 435/287.2 |
| 2004/0065655 | A1 | * | 4/2004 | Brown et al. ................ 219/428 |
| 2006/0087911 | A1 | * | 4/2006 | Herz et al. ........................ 366/101 |
| 2009/0165326 | A1 | | 7/2009 | Hedberg |
| 2010/0101109 | A1 | * | 4/2010 | Hedberg et al. ............... 34/487 |
| 2010/0132214 | A1 | * | 6/2010 | DuVal et al. ................ 34/389 |
| 2010/0326604 | A1 | * | 12/2010 | Hedberg ........................ 159/16.1 |

FOREIGN PATENT DOCUMENTS

| | | |
|---|---|---|
| EP | 1720011 A1 * | 11/2006 |
| WO | WO 2006017737 A2 * | 2/2006 |

OTHER PUBLICATIONS

Hedberg, Herbert J., "Accelerated Evaporation Process and Apparatus Utilizing Re-Circulating Loops", U.S. Appl. No. 61/220,236, filed Jun. 25, 2009, 16 pages.

* cited by examiner

*Primary Examiner* — Steve M Gravini
(74) *Attorney, Agent, or Firm* — Cesari and McKenna, LLP

(57) ABSTRACT

A covered sample plate with wells holding samples to be dried. The cover has through holes that communicate with only a portion of each well. The covered plate is inserted into a cradle of an assembly of cradles that is rotated. The cradle assembly fits into a tub and when rotated the cradles present a sold wall that functions as a centrifugal fan that drives air out through an opening in the tub. The air is dried of solvent and re-circulated back through the through holes in the cover to the sample wells.

7 Claims, 6 Drawing Sheets

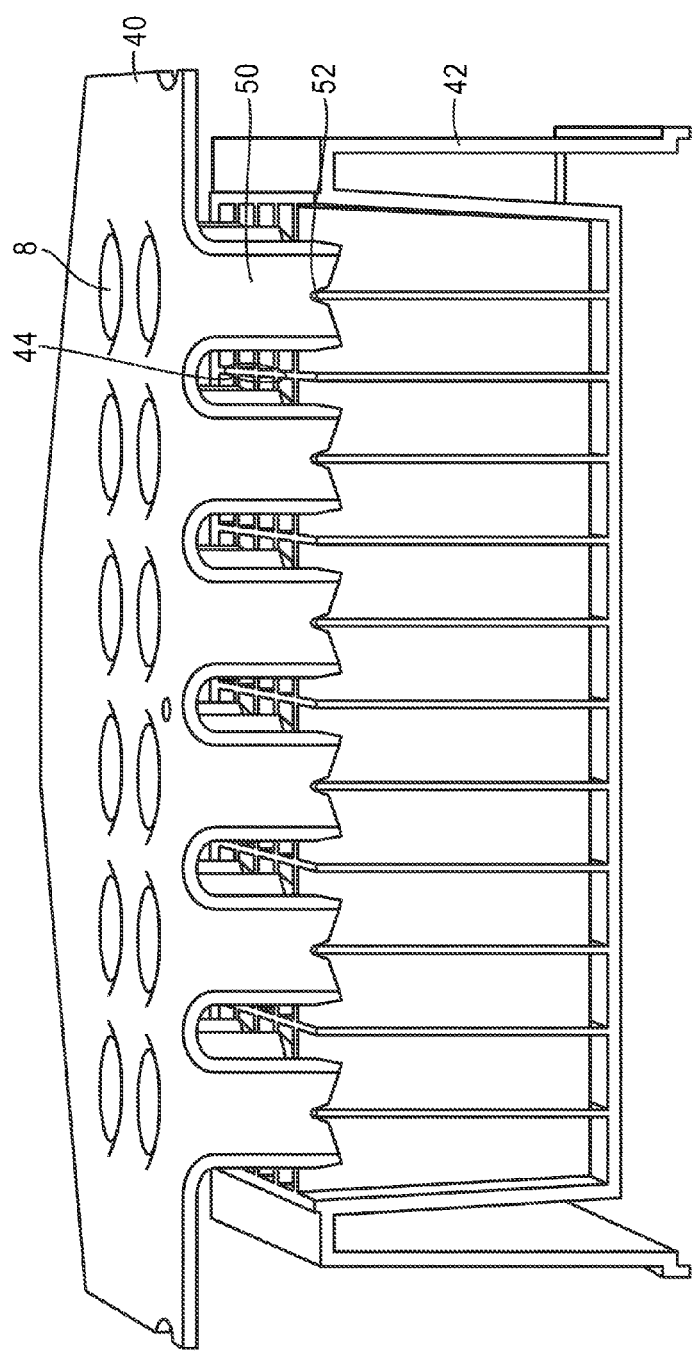
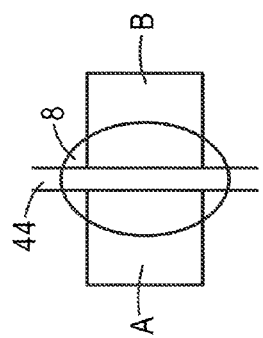
FIG. 4A
FIG. 4B

ACCELERATED EVAPORATION PROCESS AND APPARATUS UTILIZING RE-CIRCULATING LOOPS

RELATED APPLICATIONS

The present application is related to and claims priority from a provisional patent application of common title, inventorship and ownership as the present application. That provisional application was filed on Jun. 25, 2009, bears the Ser. No. 61/220,236, and is hereby incorporated herein by reference.

The present application is also related to an earlier application Ser. No. 12/038,405, filed Feb. 27, 2008 and published Jul. 2, 2009, entitled Apparatus and Method for Drying a Solid of Liquid Sample. This patent application is hereby incorporated herein by reference. In particular, this patent application describes mechanisms that are to be driven by the centrifugal pump with blades that drive drying air into test tubes of sample bearing liquids and then re-circulates that air (now carrying the liquid vapor) via heaters and cold traps back into the test tubes to finally dry the sample. These mechanisms may be used in examples of the present application.

BACKGROUND

1. Field

The present disclosure relates to an apparatus and a method for increasing evaporation rates of solutions within sample containers or wells by drying air flowing into the sample container. Herein after "air" is defined to include any gas, including atmospheric air, that may be used for drying samples.

2. Background Information

Sample concentrators are prevalent in processing liquid solutions containing a sample material or materials of interest. Materials of interest are typically synthesized, modified, and purified, in solution-based process steps. To recover these dissolved non-volatile materials as dry powders, or to increase the concentration of compounds, vacuum centrifuges, freeze drying, and blow down concentrators are commonly used.

Vacuum concentrators and freeze dryers generally require a powerful vacuum pump to produce the low levels of ambient pressure necessary to promote the ejection and escape of solvent molecules from the surface of the solution. These solvent molecules migrate to the lower concentration region of a cold trap solvent collection container and condense into liquid and/or freeze into ice.

Blow-down concentrators generally create a continuous flow of a small amount of air onto the surface of the liquid solution. The air flow may promote the escape of solvent molecules from the solution container that are then carried away in the flow of air out an exhaust port. Flow rates may be typically 1 or 2 liters/minute to prevent loss of solution or dry compound from the sample container.

In one example a jet of blow-down air is directed into the opening of test tube containing liquid to be evaporated. Due to the form factor of a test tube, the incoming and exiting streams of air occupy the same region, turbulent interaction occurs, and the air may exit without nearing the liquid surface. A laminar high volume flow of blow-down air striking the surface of the liquid is the goal, but it may not be achieved due to the turbulence.

SUMMARY

In the present application test tubes are replaced by a sample plate of samples in a deep or shallow well. A cover that directs drying air is placed covering the sample plate, and the covered sample plate is placed into a cradle. The cover has through openings that communicate with only a portion of the well opening and direct air down a wall of the well to the liquid sample. The cover directs and accepts the exiting air (carrying vapor from the liquid in the well) out via a different path. Exiting air flow is isolated from the incoming air to facilitate efficient sample drying. The exiting air travels along the under side of the cover and exits the cover/microtiter plate assembly. The cradle with an inserted covered sample plate has an opening that accepts air from the underside of the cover. There is an opening in the side of the cradle that leads to a pocket formed between a closed side of the adjacent cradle and a tub encasing the cradles. This exiting air is captured in the pocket and driven out by the closed side of the adjacent cradle when the pocket passes an exhaust tube opening on the side of a tub.

The closed side of the adjacent cradles functions as centrifugal fan blades that drives the drying air in a closed loop. A similar centrifugal fan is illustrated in the above incorporated by referenced patent applications.

The present disclosure includes a cover for a sample plate holding samples in wells having well openings. The cover has a top surface and a bottom surface where the cover extends covering the sample plate. The cover has through openings allowing drying air access from the top surface to the well openings. There are extensions that descend from the bottom surface that are positioned so that the through openings align and communicate with a portion of each well opening. The extensions form channels, between the cover's bottom surface and the plate, that run from an external opening to the portion of the well openings that are not aligned with the through openings. Wherein air enters the portion of the well openings that are aligned with the through openings and interacts with the samples in the wells and exits through the portion of the well openings that are not aligned with the through openings. The air travels via the channels and exits via the external opening.

The present disclosure includes for a process that mirrors the apparatus c disclosed. The process includes the drying of samples contained in wells of a sample plate. The wells have a well opening that communicates with through holes in a cover. Air is channeled via the through holes into the wells via a first portion of the well openings. The air is directed from a second portion of the well openings that are not aligned with the through openings to an external opening that is separate from the through holes.

BRIEF DESCRIPTION OF THE DRAWINGS

The invention description below refers to the accompanying drawings, of which:

FIG. 4A is a side view detail of the cover and the sample plates;

FIG. 4B illustrates the arrangement of the through holes in the cover to the wells in the plate.

DETAILED DESCRIPTION OF AN ILLUSTRATIVE EMBODIMENT

Figure 1A:
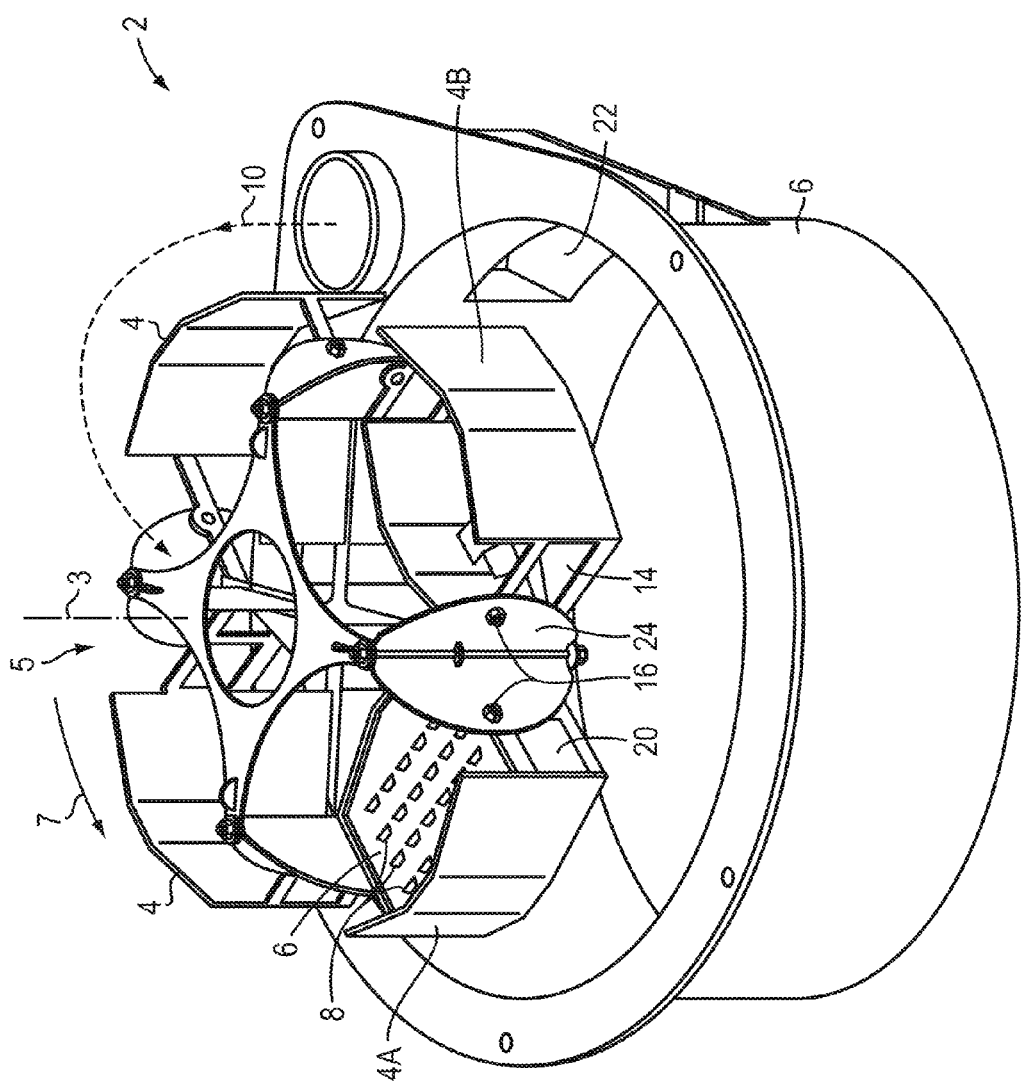
FIGS. 1A and 1B are elevation drawings of a four cradle rotor bearing a covered sample plate and the enclosing tub, the rotating four cradle rotor forms a centrifugal fan.

FIG. 1A illustrates a four cradle rotor 2 with four cradles 4 that extend from a center opening 5 on a vertical axis 3. One cradle 4A has a covered microtiter plate 6 inserted. The cradles are horizontal allowing the covered microtiter plates to be loaded. The four cradle rotor 2 is shown above a tub 6 into which it fits when it is lowered.

Figure 1B:
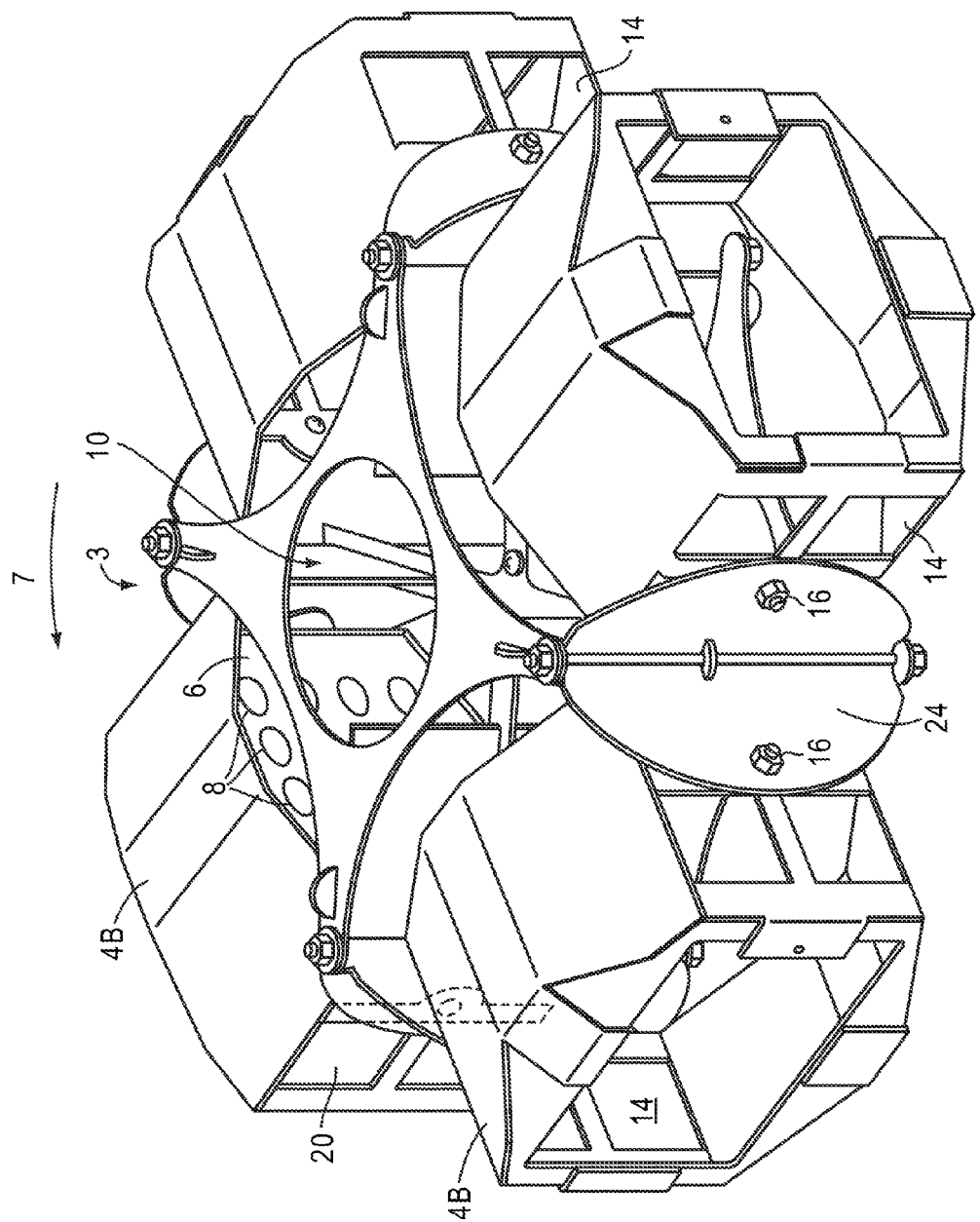

In FIG. 1A there is a drive mechanism (not shown) that rotates the four cradle rotor 2 in the direction 7. Drying air is driven out the opening 22 along the path 10. That path includes returning to the center opening, the axis 5, where it is driven by the four cradle rotor 2 acting as a centrifugal fan horizontally driving air. FIG. 1B illustrates the four cradle rotor 2 when rotating at speed. Here the cradle 4A holding the through the covered microtiter plate 6 and the empty cradles are vertical. The air flow 10 is down the center and out through channeled through the openings 8 in the covered microtiter plate 6, into the sells (not shown), out through the opening 22 in the tub (FIG. 1A) and back 10 to the center 5 of the four cradle rotor. When rotating at full speed the cradles are hinged, gimbaled 16 and/or weighted so that they will traverse from horizontal to vertical as illustrated in FIG. 1B.

In the return path 10 there may be a heater, a cold trap, and the necessary tubing (not shown) to return the drying air to the center opening 5 of the four cradle rotor 2.

As in FIG. 1A, when the four cradle rotor is fit into the tub 6, the opening 14 of one cradle 4B faces the solid wall 20 of an adjacent cradle forming a pocket 24 or corner where the air exiting a cradle is trapped. That air is driven out from the tub 6 when the pocket reaches an opening 22 in the wall of the tub.6. Note the cradles in FIG. 1A will be vertical as shown in FIG. 1B, not horizontal as in FIG. 1A.

The drying configuration of a covered microtiter plate 6 may contain ninety six sample wells, each with a volume of 2.2 milliliters. When spinning, the covered microtiter plates swing up from their horizontal position as in FIG. 1A to the vertical as in FIG. 1B.

FIG. 1A shows a covered microtiter plate 6 in cradle 4A. The opening 14 in the side of the cradle 4B is opposite the solid face 20 of the covered microtiter plate 6. When inserted into the tub 6 and at rotating speed the solid face 20 forms a fan blade that traps air in the pocket 24 between the cradles 4A and 4B and the wall of the tub 6 and drives it out the tub opening 22.

Figure 2:
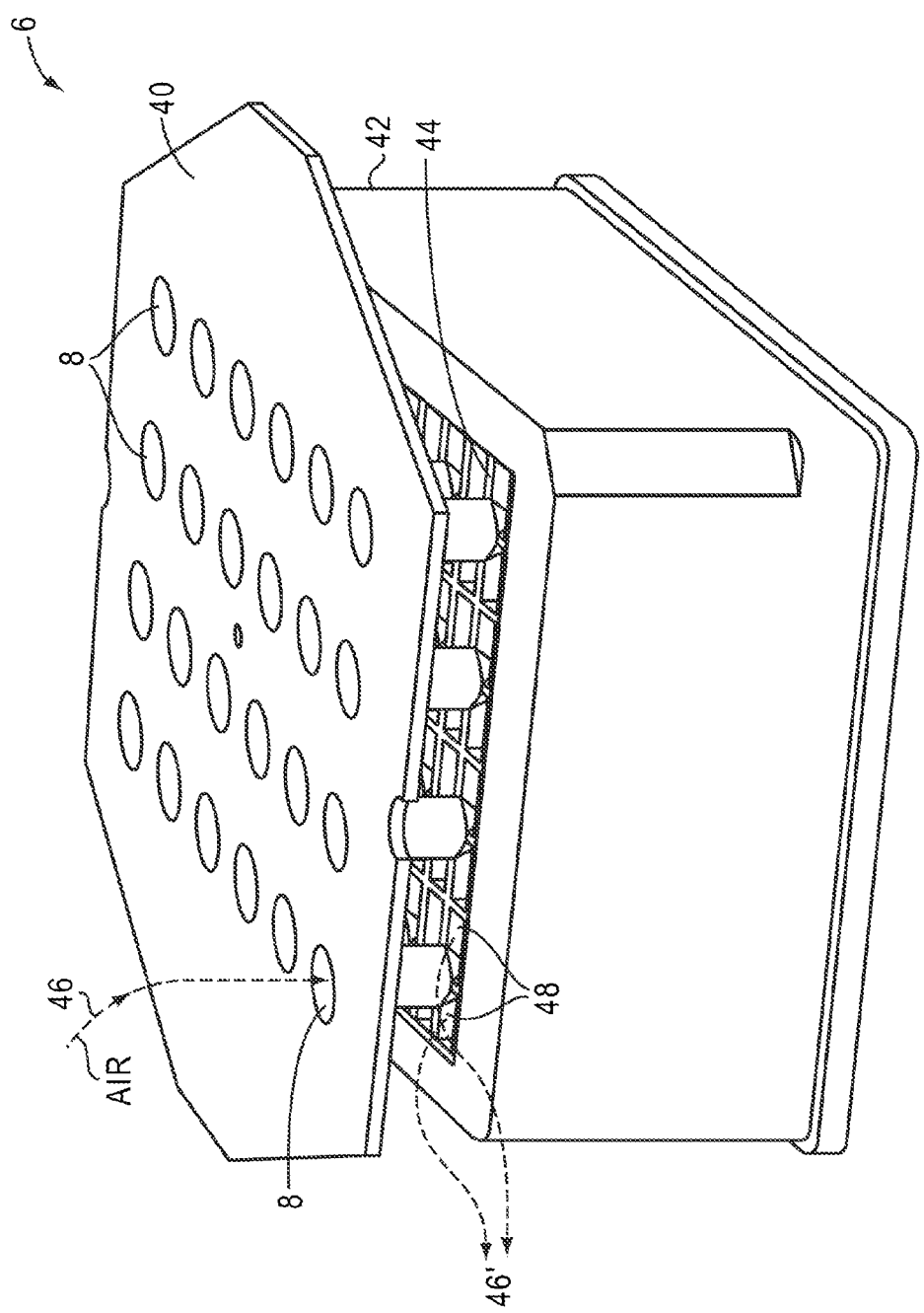
FIG. 2 is an illustration of a covered sample plate.

FIG. 2 shows an elevation view the covered microtiter plate 6 with a cover 40 and the microtiter plate 42. Drying air is driven 46 into the openings 8, into the sample wells 44, back up out of the wells 44, hitting the bottom of the cover 40 that channels the air out 46' from under the cover 40. This air flow is shown as the path 46 into the cover openings 8, down into, in this case, two wells 48, up and out from the wells 48 and exiting 46' beneath the cover as illustrated.

Figure 3:
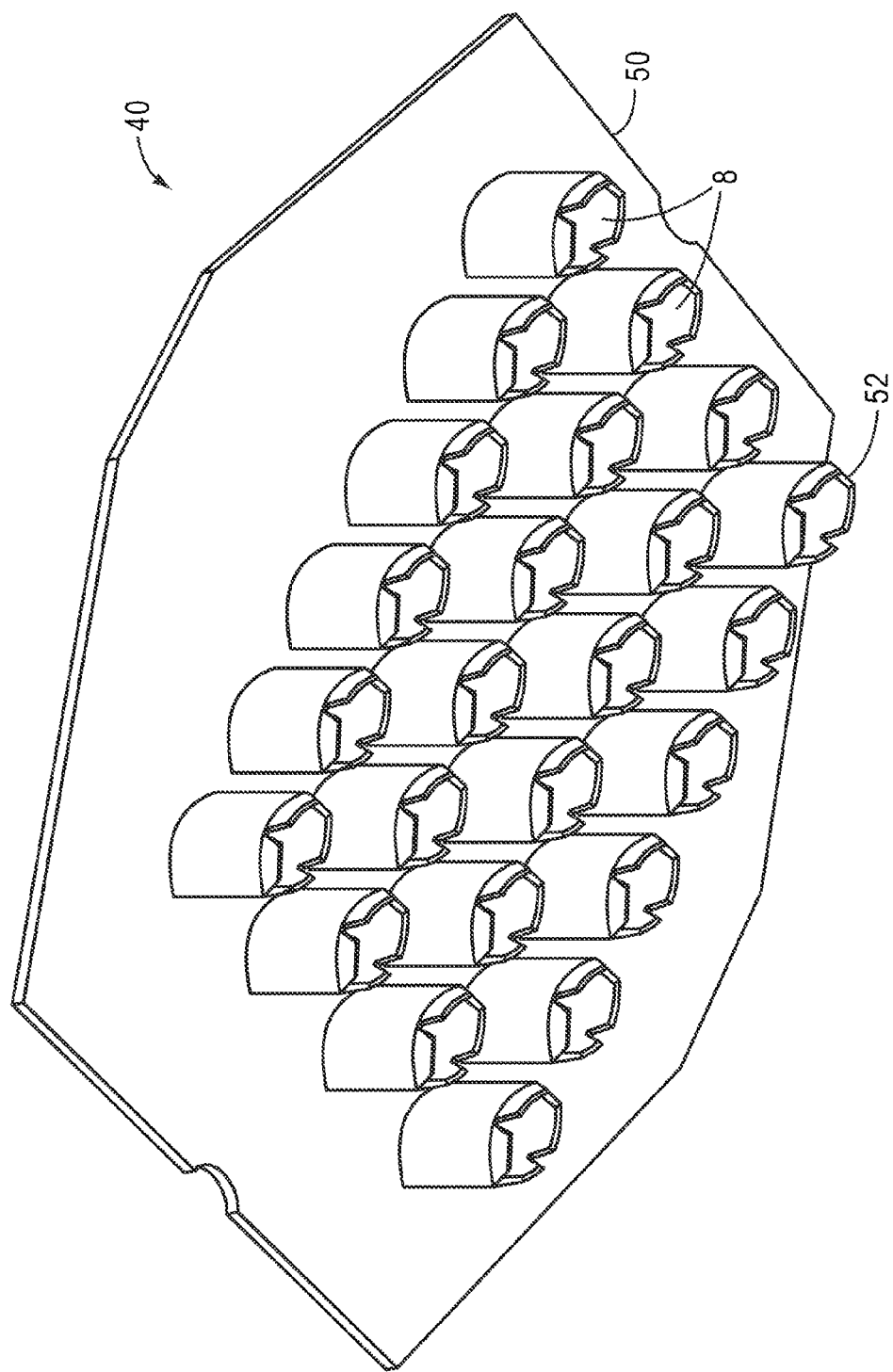
FIG. 3 a an elevation view of the bottom of an illustrative sample plate cover.

FIG. 3 shows the cover 40 from below. Each through hole 8 has an extension 50 that descends from the cover 40 with slots 52 at the extremities of the extensions 50. FIG. 4A shows the microtiter plate 42, the cover 40 and the extensions 50 that are configured to fit over well separators 44. Note that each through hole 8 extension 50 communicates with two wells A and B of FIG. 4B, although in other examples more than two wells may communicate with each through hole 8.

Figure 5:
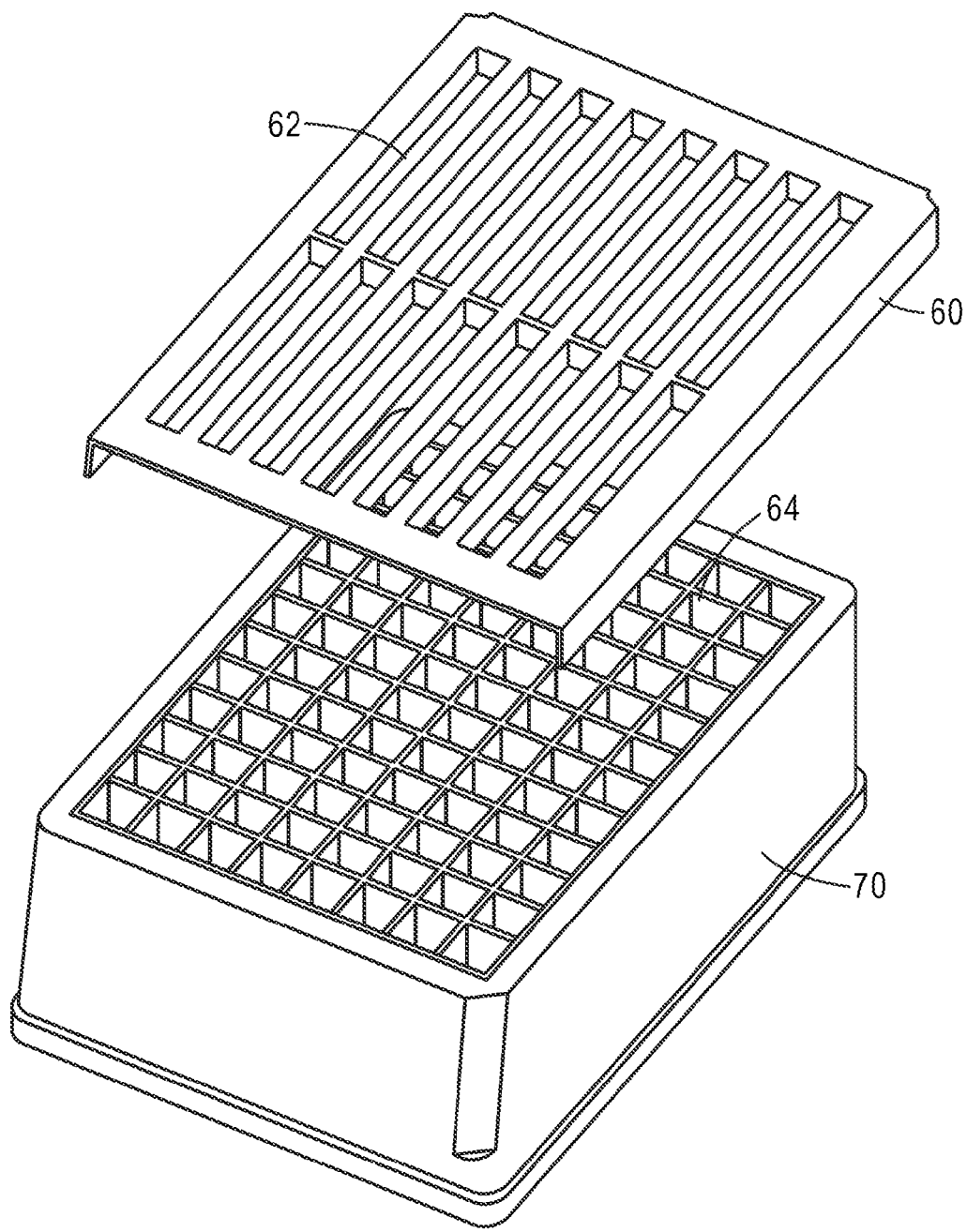
FIG. 5 illustrates an alternative type of cover and sample plate.

FIG. 5 shows an alternative illustration of covered microtiter plate. Here the cover 60 has flaps along the edges except for one side, and the through holes 62 are slots communicating with many wells 64.

What is claimed is:

1. A cover for a sample plate holding samples in wells having well openings, the covered plate comprising:
    a top surface and a bottom surface, the cover extends covering the sample plate;
    through openings allowing access from the top surface to the well openings; and extensions that descend below the bottom surface, the extensions positioned so that the through openings align and communicate with a portion of each well opening; and wherein the extensions form channels between the bottom surface and the plate, the channels running from an external opening to the portion of the well openings that are not aligned with the through openings, wherein gas enters the well openings that are aligned with the through openings and interacts with the samples in the wells and exits through the portion of the well openings not aligned with the through openings, and travels via the channels and exits via the external opening.

2. The covered plate of claim 1 wherein each through opening communicates with more than one well.

3. A cradle arranged for carrying a sample plate covered by the cover of claim 1, wherein the cradle assembly has one side with an opening that aligns with the external opening, and a second side that is a flat solid surface.

4. An assembly of a plurality of cradles of claim 3, wherein the plurality of cradles are fastened together in a circular fashion suitable for rotating, wherein when the assembly is rotating, the second flat solid side of the cradle functions as a blade of a centrifugal fan.

5. The assembly of claim 4 further comprising a tub into which the assembly fits, the tub having a circular wall that surrounds the assembly, the circular wall having an opening positioned to receive gas exiting from the external opening.

6. A process for drying samples contained in wells of a sample plate, the respective wells having well openings, the process comprising the steps of:
    covering the sample plate with a cover having through holes and extensions that descend from a bottom surface of the cover;
    directing gas via the through holes into the wells via first portions of the respective well openings; and
    directing gas from second portions of the respective well openings to an external opening that is separate from the through holes via channels that are associated with the extensions.

7. The process of claim 6 further comprising the step of channeling gas from one through hole into the first portion of one well opening.

* * * * *